United States Patent [19]

Lee

[11] Patent Number: 5,643,223
[45] Date of Patent: Jul. 1, 1997

[54] MEDICINAL DISPENSER

[76] Inventor: Richard K. Lee, 50-9, Chung-Shun Street, Chunghua City, 50013, Taiwan

[21] Appl. No.: 527,675

[22] Filed: Sep. 12, 1995

[51] Int. Cl.$^6$ .................................................. A61M 1/00
[52] U.S. Cl. .................................... 604/212; 604/111
[58] Field of Search ........................... 604/212, 213, 604/215, 216, 217, 187, 110, 111

[56] References Cited

U.S. PATENT DOCUMENTS

| | | | |
|---|---|---|---|
| 1,490,966 | 4/1924 | Dell | 604/212 X |
| 2,848,997 | 8/1958 | Miskel et al. | 604/212 X |
| 4,508,534 | 4/1985 | Garver, Sr. et al. | 604/111 |
| 4,752,288 | 6/1988 | Hussey | 604/111 |

OTHER PUBLICATIONS

Brochure for OcuCoat™ PF Lubricating Eye Drops, Aug. 1993.

*Primary Examiner*—John D. Yasko
*Attorney, Agent, or Firm*—Fish & Richardson P.C.

[57] ABSTRACT

A medicinal dispenser features a reservoir having an internal volume for supporting a liquid, a neck portion extending from the internal volume to a distal tip having an opening for dispensing the liquid from the reservoir, and a removable cover having a cap portion for sealing the opening when the cover is securely positioned over the reservoir. The medicinal solution dispenser is structured to protect the orifice, from which solution flows from the dispenser, as well as portions proximate to the orifice, from contaminants in the air or from manual contact.

5 Claims, 2 Drawing Sheets

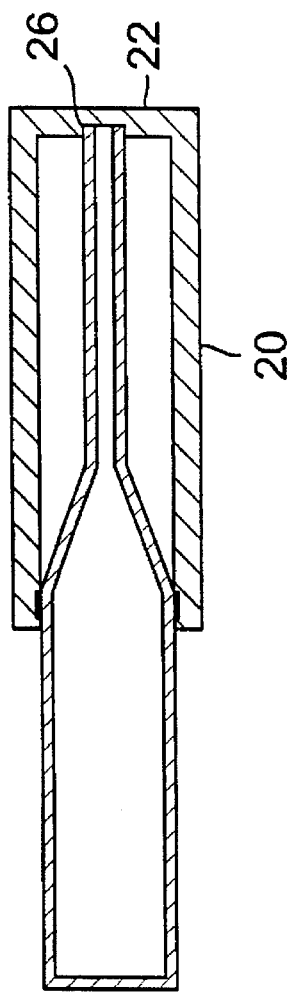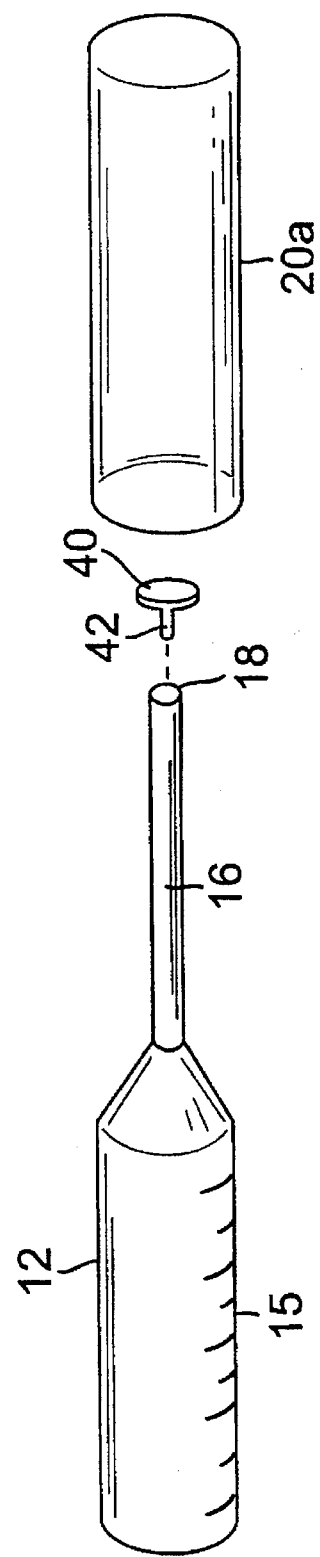

MEDICINAL DISPENSER

BACKGROUND OF THE INVENTION

Some medicinal solutions (e.g., eyedrops) and ointments are dispensed from small, disposable, single-dose plastic packets or containers. The solution is generally sealed within the containers by a portion which is removed (e.g., torn along a serrated line) and disposed of. After the solution is dispensed from the packet the remaining portion of the packet is thrown away.

SUMMARY OF THE INVENTION

The present invention relates to a medicinal solution dispenser structured to protect the orifice (from which solution flows from the dispenser), as well as portions proximate to the orifice, from contaminants in the air or from manual contact. In a general aspect of the invention, a medicinal dispenser includes a reservoir member having an internal volume for supporting a liquid, a neck portion extending from the internal volume to a distal tip having an opening for dispensing the liquid from the reservoir member, and a removable cover having a cap portion for sealing the opening when the cover is securely positioned over the reservoir member.

The removable cover may include a sleeved portion having an open end sized and configured to receive the reservoir member. The sleeved portion extends from the cap portion so that when the cover is secured to the reservoir member, the sleeve portion encloses the length of the neck portion to protect it from external contaminants. The cover may include a protuberance formed on an inner surface of the head portion that is sized to engage and seal the opening of the neck portion when the cover is secured to the reservoir member. Alternatively, the cover may include a recessed portion which receives and seals the opening in the tip when the cover is in place. The medicinal dispenser may include frangible seals formed (e.g., by thermalforming) between the cap portion and the distal tip of the neck portion and between the open end of the sleeve portion and an outer surface of the reservoir member. Upon initial use, the frangible seals are fractured to allow removal of the cap member from the reservoir member and to provide the opening at the distal tip portion of the neck portion.

In another aspect, the medicinal dispenser includes a removable cap member having a sealing portion extending into the opening when the cap member is securely positioned over the reservoir member. The medicinal dispenser may include an optional sleeved cover to extending over the neck portion of the medicinal dispenser as well as the removable cap member.

Other features and advantages of the invention will become apparent from the following detailed description, and from the claims.

BRIEF DESCRIPTION OF THE DRAWINGS

FIG. 3 is an alternative embodiment of the medicinal dispenser and cover of FIG. 1.

FIG. 4 is a medicinal dispenser having a cap and optional cover.

DESCRIPTION OF THE PREFERRED EMBODIMENTS

Figure 1:
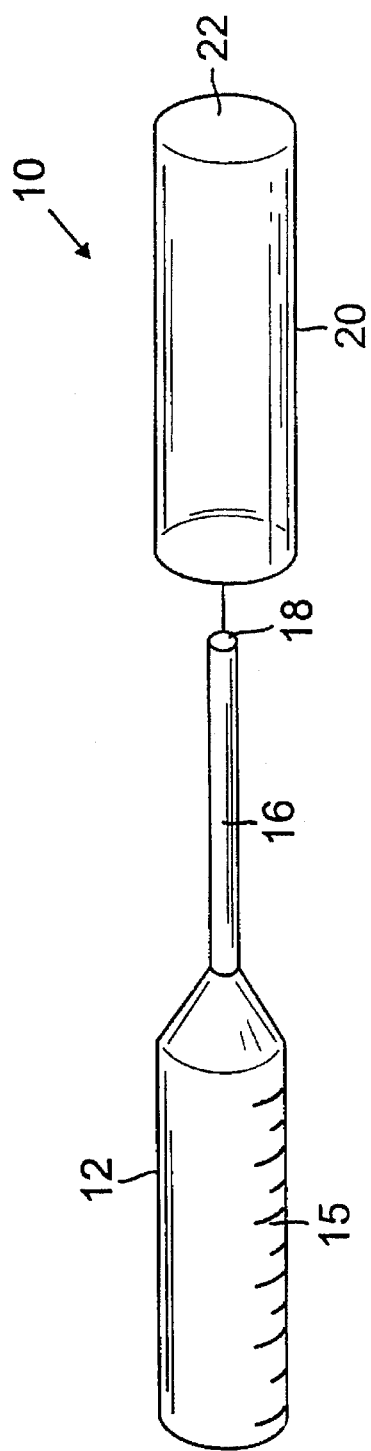
FIG. 1 is an exploded perspective view of the medicinal dispenser and cover.
Figure 2:
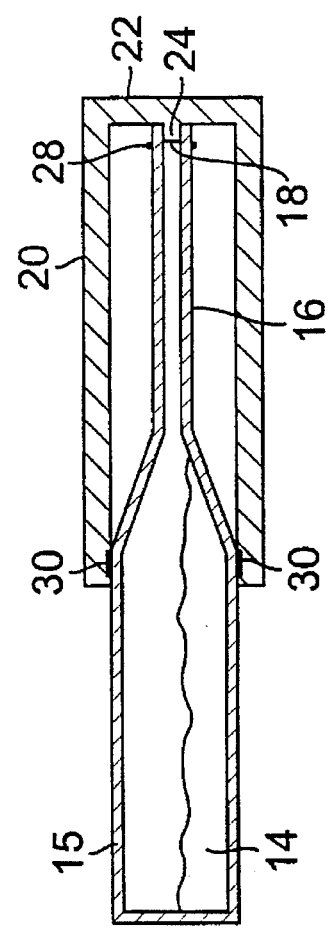
FIG. 2 is a cross-sectional side view of the medicinal dispenser and cover of FIG. 1.

Referring to FIGS. 1 and 2, a medicinal solution dispenser 10 is shown to include a cylindrically-shaped sterile plastic medicinal dispenser 12 for holding a predetermined amount of medicinal solution 14 (e.g., eyedrops, artificial tears) within a reservoir 15. Medicinal dispenser 12 has, at one end of the reservoir, a portion which necks down to an elongated slender tube 16 which extends to an opening 18 where the solution is dispensed. The size of opening 18 and length of tube 16 are largely dependent on the type of solution, the amount of solution desired to be dispensed, and where the solution is being dispensed. For example, the diameter of opening 18 is generally between 50 and 75 mils for dispensing eyedrops into the eye. Tube 16 may be longer and opening 18 larger, for example, where dispenser 10 is used to provide a medicinal suppository in the anus. Dispenser 10 further includes a sleeve-like cover 20 for enclosing tube 16. Cover 20 is sized to provide a relatively snug fit over the reservoir end of medicinal dispenser 12.

Referring to FIG. 2, cover 20 has a capped end 22 having a protuberance 24 formed on its inner surface. Protuberance 24 is sized and positioned to seal opening 18 when cover 20 is in place to prevent the flow and/or evaporation of the solution from medicinal dispenser 12.

In an alternate embodiment, shown in FIG. 3, a recession 26 is molded within capped end 22 instead of a protuberance. Here, the distal tip of tube 16 fits within the recession to seal off opening 18.

Referring again to FIG. 2, in the manufacture of dispenser 10, cover 20 is heat sealed to medicinal dispenser 12 at seal 28 where protuberance 24 contacts the distal end of tube 16. Heat sealing is also provided at spaced seals 30 around the periphery of the end opening of cover 20 where the inner surface of medicinal dispenser 12 mates with the outer surface of the cover.

When dispenser 10 is initially put to use, the user provides a sufficient force to break seals 28, 30, thereby separating cover 20 from medicinal dispenser 12. It may be necessary to provide a slight twist as the two elements are being broken apart. After the desired amount of solution is dispensed, the user can replace cover 20 over medicinal dispenser 12 to protect tube 16 and opening 18 from contaminants during handling. It is important to note that during both the dispensing of the solution and the re-sealing of medicinal dispenser 20 no manual contact of tube 16, opening 18, or protuberance 24 is necessary. Thus, the sterility of those portions of dispenser 10 can be maintained while allowing repeated use.

Referring to FIG. 4, in another embodiment, a removable stopper 40 includes a finger 42 which is inserted within opening 18 to seal the opening after each use of the dispenser. An optional cover 20a may be provided to protect elongated tube 16 leading from reservoir 15 to opening 18 as well as stopper 42.

From the above description, one skilled in the art can easily ascertain the essential characteristics of the present invention, and without departing from the spirit and scope thereof, can make various changes and modifications of the invention to adapt it to various usages and conditions. Thus, other embodiments are within the claims.

What is claimed is:

1. A medicinal dispenser comprising:
   a reservoir member having an internal volume for supporting a solution and a neck portion extending from the internal volume to a distal tip having an opening for dispensing the solution from said reservoir member;
   a cover member having a cap portion with an inner surface configured to seal said opening when said cover member is securely positioned over said reservoir member;

a sleeved portion extending from said cap portion, said sleeve portion extending over the length of said neck portion when said cover member is secured to said reservoir member, thereby protecting said neck portion from external contaminants, wherein said sleeve portion includes an open end sized and configured to sealingly engage an outer surface of said reservoir member; and a first frangible seal formed between said cap portion and said distal tip of said neck portion and a second frangible seal formed between said open end of said sleeve portion and an outer surface of said reservoir member, wherein said first and second frangible seals are fractured to allow removal of said cover member from said reservoir member and to provide said opening at said distal tip portion of said neck portion.

2. The medicinal dispenser of claim 1 wherein said first and second frangible seals are thermalformed.

3. The medicinal dispenser of claim 1 wherein said second frangible seal is formed along a plurality of spaced regions around a periphery of said open end of said sleeve portion of said cover member.

4. A medicinal dispenser comprising:

a reservoir member having an internal volume for supporting a liquid medicant;

a neck portion extending from the internal volume to a distal tip having an opening for dispensing the liquid medicant from said reservoir member;

a removable cover member including a sealing portion extending into said opening when said cover member is securely positioned over said reservoir member;

a sleeved portion extending from said sealing portion and when said cover member is secured to said reservoir member, said sleeve portion extends over the length of said neck portion thereby protecting said neck portion from external contaminants, wherein said sleeve portion includes an open end sized and configured to sealingly engage an outer surface of said reservoir member; and a first frangible seal formed between said sealing portion and said distal tip of said neck portion and a second frangible seal formed between said open end of said sleeve portion and an outer surface of said reservoir member, wherein said first and second frangible seals are fractured to allow removal of said cover member from said reservoir member and to provide said opening at said distal tip portion of said neck portion.

5. The medicinal dispenser of claim 4 wherein said second frangible seal is formed along a plurality of spaced regions around a periphery of said open end of said sleeve portion of said cover member.

* * * * *